//  (12) United States Patent
Michaelis et al.

(10) Patent No.: US 7,524,887 B2
(45) Date of Patent: Apr. 28, 2009

(54) 2-AMINO-1,3-PROPANEDIOL COMPOUNDS FOR THE TREATMENT OF ACUTE PAIN

(75) Inventors: Martin Michaelis, Frankfurt (DE); Gerd Geisslinger, Bad Soden (DE); Klaus Scholich, Dreieich (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 679 days.

(21) Appl. No.: 10/853,761

(22) Filed: May 25, 2004

(65) Prior Publication Data
US 2004/0248988 A1 Dec. 9, 2004

Related U.S. Application Data

(60) Provisional application No. 60/510,994, filed on Oct. 14, 2003.

(30) Foreign Application Priority Data
Jun. 6, 2003 (EP) .................... 03012864

(51) Int. Cl.
A61K 31/137 (2006.01)
A61K 31/131 (2006.01)
A61K 31/132 (2006.01)
C07C 215/10 (2006.01)
C07C 215/20 (2006.01)
C07C 217/28 (2006.01)
C07C 217/44 (2006.01)
C07C 219/06 (2006.01)
C07C 219/04 (2006.01)
C07C 219/18 (2006.01)

(52) U.S. Cl. ................. 514/653; 514/667; 564/360; 564/503; 564/507

(58) Field of Classification Search .......... 514/255, 514/357, 427
See application file for complete search history.

(56) References Cited

U.S. PATENT DOCUMENTS
5,604,229 A * 2/1997 Fujita et al. ............. 514/252.1

FOREIGN PATENT DOCUMENTS
EP          0 627 406 A1   12/1994
EP          0 812 588 A1   12/1997
EP          1 002 792 A1   5/2000
EP          1 050 301 A1   11/2000
FR          2 249 653      5/1975
WO          WO 98/22100    5/1998

OTHER PUBLICATIONS

The American Heritage College Dictionary,3rd Edition, 1993, p. 1097.*
Woolf CJ et. al. The Lancet (353) 1959-1964, 1999.*
Cain et. al. Physiology & Behavior (62) 199-205, 1997.*
Merck Manual of Diagnostics, 17th Edition, 1999, pp. 1363-1376.*
Ugolini et. al. PNAS, 2007, 104(8), 2985-2990.*
Ueda et. al. Pharmacology & Therapeutics, 2006, 109, 57-77.*
Hochberg et. al. The American Journal of Managed Care, Nov. 2002, S502-517.*
Kahan B.D., Sirolimus and FTY720: new approaches to transplant immunosuppression, Transplantation Proceedings, vol. 34, No. 7, Nov. 2002, pp. 2520-2522.
Kluk M.J. et al, Signaling of sphingosine-1-phosphate via the S1P/EDG-family of G-protein-coupled receptors, Biochim Biophys Acta 1582, 2002, pp. 72-80.
Schaible H.G. et al et al., How do we manage chronic pain?, Baillieres Best. Pract. Res. Clin. Rheumatology, vol. 14, No. 4, Dec. 2000, pp. 797-811.
Spiegel S. et al, Sphingosine 1-Phosphate, a Key Cell Signaling Molecule, J. Biol. Chem., vol. 277, No. 29,2002, pp. 25851-25854.

* cited by examiner

Primary Examiner—Shaojia Anna Jiang
Assistant Examiner—Eric S Olson
(74) Attorney, Agent, or Firm—Irving Newman; Craig M. Bell; Paul R. Darkes

(57) ABSTRACT

The present invention relates to a method for the prophylaxis or treatment of pain using compounds of formula I,

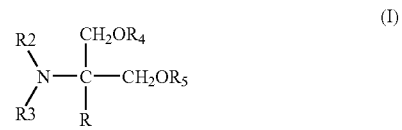

in which R, R2, R3, R4 and R5 have the meanings indicated in the specification.

12 Claims, No Drawings

US 7,524,887 B2

2-AMINO-1,3-PROPANEDIOL COMPOUNDS FOR THE TREATMENT OF ACUTE PAIN

CROSS-REFERENCE TO RELATED APPLICATIONS

This application claims the benefit of priority of European Application 03012864.9, filed Jun. 6, 2003, as well as the benefit of U.S. Provisional Application No. 60/510,994, filed Oct. 14, 2003.

SUMMARY OF THE INVENTION

The present invention relates to the use of compounds of formula I,

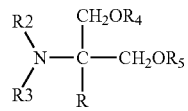

in which R, R2, R3, R4 and R5 have the meanings indicated below, for the preparation of pharmaceuticals for the prophylaxis or treatment of various types of pain.

BACKGROUND

Compounds of formula I are described in EP 0 627 406 as medicaments for immunosuppression, suppressing rejection, autoimmune diseases, rheumatoid arthritis, psoriasis, atopic dermatitis, bronchial asthma, pollinosis or Behcet's disease.

Pain is a complex subjective sensation reflecting real or potential tissue damage and the affective response to it. Acute pain is a physiological signal indicating a potential or actual injury. Chronic pain can either be somatogenic (organic) or psychogenic. Chronic pain is frequently accompanied or followed by vegetative signs, which often result in depression.

Somatogenic pain may be of nociceptive origin, inflammatory or neuropathic. Nociceptive pain is judged to be commensurate with ongoing activation of somatic or visceral pain-sensitive nerve fibers. Neuropathic pain results from dysfunction in the nervous system; it is believed to be sustained by aberrant somatosensory processes in the peripheral nervous system, the central nervous system (CNS), or both. (For an overview of pain mechanisms, see, for example, Scholz and Woolf, 2002; Julius and Basbaum, 2001, Woolf and Mannion, 1999; Wood, J. D., 2000; Woolf and Salter, 2000.)

Chronic pain results in individual suffering and social economic costs of tremendous extent. Existing pharmacological pain therapies are widely unsatisfying both in terms of efficacy and of safety.

Up to now, two classes of analgesics were mainly employed for the treatment of pain: Non-opioid analgesics, mostly acetaminophen and NSAIDS (non-steroidal anti-inflammatory drugs) and opioid (narcotic) agonists (wherein "opioid" is a generic term for natural or synthetic substances that bind to specific opioid receptors in the CNS, producing an agonist action). Unfortunately both analgesic classes, opioids and non-opioids, have several unwanted side effects. The most serious side effects of opioids are the possibility of inhibition of the respiratory system and, after long-term treatment, the possibility of addiction (Schaible H. G., Vanegas H.: How do we manage chronic pain? Baillieres Best. Pract. Res. Clin. Rheumatol. 2000 December; 14(4):797-811). NSAIDs, a major class of non-opioids, on the other hand, can induce a variety of gastrointestinal complications such as ulcers and bleeding, but also kidney damage (Schaible H. G., Vanegas H., 2000). It has been estimated that, in the U.S.A., about 16,000 patients die every year because of severe gastrointestinal complications caused by conventional NSAIDs.

In light of the severe drawbacks connected with state of the art pain treatments, there is a great need for novel classes of pain modulating drugs. Especially in light of the vast gap between the fast advancing understanding of the neurobiology of pain and the unmet clinical need to provide effective treatments without the drawbacks of state of the art treatments, efforts need to be directed to the discovery of new targets for novel classes of analgesics.

It was found that sphingosine-1-phosphate (S1P) is involved in nociceptive processing and is able to decrease pain. S1P is able to interact with at least one S1P receptor, activates the receptor and lowers intracellular cyclicadenosine mono phosphate (AMP). S1P can bind to a family of five G-Protein-coupled receptors, S1P1-5, also known as Endothelial Differentiation Gene receptor EDG 1, 3, 5, 6 and 8. Members of the S1P-receptor family regulate functions involved in neural cell morphology, tumor cell invasiveness, cell proliferation, angiogenesis, vascular maturation, and inhibition of neutrophil motility and migration (Kluk M. J. and Hla T. (2002), Biochim Biophys Acta 1582, 72-80; Spiegel S, and Milstien S. (2002), J Biol Chem 277, 25851-25854). It is well known that several of these actions are mediated at least in part by the inhibition of cAMP synthesis. S1P achieves its adenylate cyclase (AC) inhibitory actions by activating PAM and the inhibitory G-protein Gi. S1P treatment results in a change of the cellular localization of PAM and inhibition of AC enzyme activity. The compounds of formula I and S1P are both S1P-receptor agonists. Therefore, the compounds of formula I can be used for treatment of pain.

DETAILED DESCRIPTION

The present invention satisfies the above needs by providing compounds of formula I, for pain inhibitory activity with fewer side effects than previously employed pain relievers.

Thus, the present invention relates to a method for the prophylaxis or treatment of chronic or acute pain by administering to a patient in need thereof an effective amount of a 2-amino-1,3-propanediol compound of formula I-4

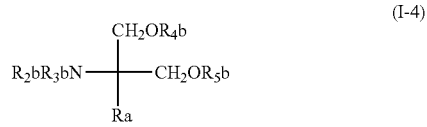

wherein:
Ra is a straight- or branched chain alkyl having 12 to 22 carbon atoms, said alkyl chain being unsubstituted or substituted in the chain by a substituent selected from the group consisting of double bonds, triple bonds and hetero atom-containing substituents selected from oxygen, sulfinyl, sulfonyl, sulfur, —N(R6)- where R6 is selected from hydrogen, acyl, alkoxycarbonyl, alkyl and aralkyl:
said alkyl chain being optionally further substituted by one or more of acyl, acylamino, alkenyloxy, alkoxy, alkoxycarbonyl, alkoxycarbonylamino, alkylamino, alkylcarbamoyl, alkylthio, alkynyloxy, amino, aralkyloxy, aralkyloxyacyloxy, carboxyl, halogen, hydroxyl, hydroxyimino and nitro; and R2b, R3b, R4b and R5b are the same or different and each is selected from hydrogen, acyl and alkyl;

or a pharmaceutically acceptable salt thereof.

The invention also relates to such method wherein the 2-amino-1,3-propanediol compound is of the formula I-8,

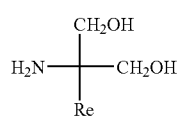
(I-8)

wherein
Re is a phenylalkyl wherein the alkyl moiety is a straight- or branched chain having 6 to 20 carbon atoms; a phenylalkyl, wherein the alkyl moiety is a straight- or branched chain alkyl having 1 to 30 carbon atoms, said phenylalkyl being substituted by a straight- or branched chain C6-C20 alkyl optionally substituted by halogen, a straight- or branched chain C6-C20 alkoxy optionally substituted by halogen, a straight- or branched chain C6-C20 alkenyloxy, phenylalkoxy, halophenylalkoxy, phenylalkoxyalkyl, phenoxyalkoxy or phenoxyalkyl; a cycloalkylalkyl wherein the alkyl moiety is a straight- or branched chain having 6 to 20 carbon atoms; a cycloalkylalkyl substituted by a straight- or branched chain alkyl having 6 to 20 carbon atoms; a heteroarylalkyl wherein the alkyl moiety is a straight- or branched chain having 6 to 20 carbon atoms; a heteroarylalkyl substituted by a straight- or branched chain alkyl having 6 to 20 carbon atoms; a heterocyclic alkyl wherein the alkyl moiety is a straight- or branched chain having 6 to 20 carbon atoms; or a heterocyclic alkyl substituted by a straight- or branched chain alkyl having 6 to 20 carbon atoms;

wherein the alkyl moiety may have, in the carbon chain, a bond or a hetero atom selected from a double bond, a triple bond, oxygen, sulfur, sulfonyl, —N(R6)- (where R6 is hydrogen, alkyl, aralkyl, acyl or alkoxycarbonyl), and carbonyl, and may have as a substituent, alkoxy, alkenyloxy, alkynyloxy, aralkyloxy, acyl, alkylamino, alkylthio, acylamino, alkoxycarbonyl, alkoxycarbonylamino, acyloxy, alkylcarbamoyl, nitro, halogen, amino, hydroxy or carboxy; or a pharmaceutically acceptable salt thereof.

The invention also relates to such method wherein the 2-amino-1,3-propanediol compound is of formula I-9,

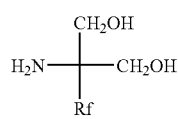
(I-9)

wherein:
Rf is a phenylalkyl wherein the alkyl moiety is a straight- or branched chain having 6 to 20 carbon atoms which may have, in the carbon chain, one or two oxygen atoms; a phenylalkyl, wherein the alkyl moiety is a straight- or branched chain alkyl having 1 to 30 carbon atoms, said phenylalkyl being substituted by a straight- or branched chain C6-C20 alkyl optionally substituted by halogen, a straight- or branched chain C6-C20 alkoxy optionally substituted by halogen, a straight- or branched chain C6-C20 alkenyloxy, phenylalkoxy, halophenylalkoxy, phenylalkoxyalkyl, phenoxyalkoxy or phenoxyalkyl; a cycloalkylalkyl wherein the alkyl moiety is a straight- or branched chain having 6 to 20 carbon atoms which may have, in the carbon chain, one or two oxygen atoms; a cycloalkylalkyl substituted by a straight- or branched chain alkyl having 6 to 20 carbon atoms; a heteroarylalkyl wherein the alkyl moiety is a straight- or branched chain having 6 to 20 carbon atoms which may have, in the carbon chain, one or two oxygen atoms; a heteroarylalkyl substituted by a straight- or branched chain alkyl having 6 to 20 carbon atoms; a heterocyclic alkyl wherein the alkyl moiety is a straight- or branched chain having 6 to 20 carbon atoms which may have, in the carbon chain, one or two oxygen atoms; or a heterocyclic alkyl substituted by a straight- or branched chain alkyl having 6 to 20 carbon atoms;

wherein the alkyl moieties have in the carbon chain a substituent selected from alkoxy, alkenyloxy, alkynyloxy, aralkyloxy, acyl, alkylamino, alkylthio, alkoxycarbonyl, alkoxycarbonylamino, acyloxy, alkylcarbamoyl, nitro, halogen, amino, hydroxy and carboxy; or a pharmaceutically acceptable salt thereof.

The invention also relates to such method wherein the 2-amino-1,3-propanediol compound is of formula I-10,

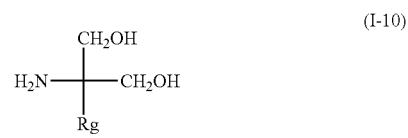
(I-10)

wherein
Rg is a phenylalkyl wherein the alkyl moiety is a straight- or branched chain having 6 to 20 carbon atoms which may have, in the carbon chain, one or two oxygen atoms; a phenylalkyl, wherein the alkyl moiety is a straight- or branched chain alkyl having 1 to 30 carbon atoms, said phenylalkyl being substituted by a straight- or branched chain C6-C14 alkyl optionally substituted by halogen, a straight- or branched chain C6-C14 alkoxy optionally substituted by halogen, a straight- or branched chain C6-C14 alkenyloxy, phenylalkoxy, halophenylalkoxy, phenylalkoxyalkyl, phenoxyalkoxy or phenoxyalkyl; a cycloalkylalkyl wherein the alkyl moiety has 6 to 20 carbon atoms; a cycloalkylalkyl substituted by a straight- or branched chain alkyl having 6 to 14 carbon atoms; a heteroarylalkyl wherein the alkyl moiety has 6 to 20 carbon atoms; a heteroarylalkyl substituted by a straight- or branched chain alkyl having 6 to 14 carbon atoms; a heterocyclic alkyl wherein the alkyl moiety has 6 to 20 carbon atoms; or a heterocyclic alkyl substituted by a straight- or branched chain alkyl having 6 to 14 carbon atoms; or a pharmaceutically acceptable salt thereof.

The invention also relates to such method wherein the 2-amino-1,3-propanediol compound is of formula I-12,

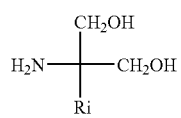

(I-12)

wherein
Ri is a phenylalkyl, wherein the alkyl moiety is a straight- or branched chain alkyl having 1 to 30 carbon atoms, said phenylalkyl being substituted by a straight- or branched chain C6-C14 alkyl optionally substituted by halogen, a straight- or branched chain C6-C14 alkoxy optionally substituted by halogen or a straight- or branched chain C6-C14 alkenyloxy,
wherein the alkyl moiety of phenylalkyl may be substituted by hydroxy, or a pharmaceutically acceptable salt thereof.

The invention also relates to said method wherein the 2-amino-1,3-propanediol compound is of formula I-13,

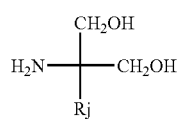

(I-13)

wherein
Rj is a phenylalkyl, wherein the alkyl moiety is a C2-C6 alkyl optionally substituted by hydroxy, said phenylalkyl being substituted by a straight- or branched chain C6-C14 alkyl optionally substituted by halogen, a straight- or branched chain C6-C14 alkoxy optionally substituted by halogen, or a straight- or branched chain C6-C14 alkenyloxy, or a pharmaceutically acceptable salt thereof.

Preferably, the 2-amino-1,3-propanediol compound is selected from the group consisting of:
2-amino-2-[2-(4-heptylphenyl)ethyl]-1,3-propanediol,
2-amino-2-[2-(4-octylphenyl)ethyl]-1,3-propanediol,
2-amino-2-[2-(4-octylphenyl)ethyl]-1,3-propanediol hydrochloride,
2-amino-2-[2-(4-nonylphenyl)ethyl]-1,3-propanediol,
2-amino-2-[2-(4-decylphenyl)ethyl]-1,3-propanediol,
2-amino-2-[2-(4-undecylphenyl)ethyl]-1,3-propanediol,
2-amino-2-[2-(4-dodecylphenyl)ethyl]-1,3-propanediol,
2-amino-2-[2-(4-tridecylphenyl)ethyl]-1,3-propanediol,
2-amino-2-[2-(4-tetradecylphenyl)ethyl]-1,3-propanediol,
2-amino-2-[2-(4-hexyloxyphenyl)ethyl]-1,3-propanediol,
2-amino-2-[2-(4-heptyloxyphenyl)ethyl]-1,3-propanediol,
2-amino-2-[2-(4-octyloxyphenyl)ethyl]-1,3-propanediol,
2-amino-2-[2-(4-nonyloxyphenyl)ethyl]-1,3-propanediol,
2-amino-2-[2-(4-decyloxyphenyl)ethyl]-1,3-propanediol,
2-amino-2-[2-(4-undecyloxyphenyl)ethyl]-1,3-propanediol,
2-amino-2-[2-(4-dodexyloxyphenyl)ethyl]-1,3-propanediol,
2-amino-2-[2-(4-tridecyloxyphenyl)ethyl]-1,3-propanediol,
2-amino-2-[2-(4-(8-fluorooctyl)phenyl)ethyl]-1,3-propanediol,
2-amino-2-[2-(4-(12-fluorododecyl)phenyl)ethyl]-1,3-propanediol,
2-amino-2-[2-(4-(7-fluoroheptyloxy)phenyl)ethyl]-1,3-propanediol,
2-amino-2-[2-(4-(11-fluoroundecyloxy)phenyl)ethyl]-1,3-propanediol and
2-amino-2-[2-(4-(7-octenyloxy)phenyl)ethyl]-1,3-propanediol, and the pharmaceutically acceptable salts thereof.

In general, the meaning of any group, residue, heteroatom, number etc., which can occur more than once in the compounds of formulae I-4, I-8, I-9, I-10, I-12 or I-13, is independent of the meaning of this group, residue, heteroatom, number etc. in any other occurrence. All groups, residues, heteroatoms, numbers etc, which can occur more than once in the compounds of formulae I-4, I-8, I-9, I-10, I-12 or I-13 can be identical or different.

As used herein, the term "alkyl having 1 to 30 carbon atoms" is to be understood in the broadest sense to mean hydrocarbon residues which can be linear, i.e. straight-chain, or branched and which can be acyclic or cyclic residues or comprise any combination of acyclic and cyclic subunits. Further, the term alkyl as used herein expressly includes saturated groups as well as unsaturated groups which latter groups contain one or more, for example one, two, three or four double bonds and/or triple bonds, provided that the double bonds are not located within a cyclic alkyl group in such a manner that an aromatic system results. All these statements also apply if an alkyl group occurs as a substituent on another residue, for example in an alkyloxy residue, an alkyloxycarbonyl residue or an arylalkyl residue. Examples of alkyl having 1 to 30 carbon atoms or alkylene having 1 to 30 carbon atoms are alkyl residues such as methyl, methylene, ethyl, ethylene, propyl, propylene, butyl, butylene, pentyl, pentylene, hexyl, heptyl, octyl, nonyl, decyl, undecyl, dodecyl, tridecyl, tetradecyl, pentadecyl, hexadecyl, heptadecyl, octadecyl, nonadecyl, icosyl, henicosyl, docosyl, tricosyl, tetracosyl, pentacosyl, hexacosyl, heptacosyl, octacosyl, nonacosyl or triacontyl. The n-isomers of all these residues, isopropyl, isobutyl, 1-methylbutyl, isopentyl, neopentyl, 2,2-dimethylbutyl, 2-methylpentyl, 3-methylpentyl, isohexyl, sec-butyl, tBu, tert-pentyl, sec-butyl, tert-butyl or tert-pentyl.

The term "alkenyl having 2 to 30 carbon atoms" is an unsaturated alkyl residue having 2 to 30 carbon atoms and contains 1, 2, 3 or 4 double bonds and can be derived from alkyl as defined above such as vinyl, 1-propenyl, 2-propenyl (=allyl), 2-butenyl, 3-butenyl, 2-methyl-2-butenyl, 3-methyl-2-butenyl, 5-hexenyl or 1,3-pentadienyl.

The term "alkynyl having 2 to 30 carbon atoms" is an unsaturated alkyl residue having 2 to 30 carbon atoms and contains 1, 2, 3 or 4 triple bonds and can be derived from alkyl as defined above such as ethynyl, 1-propynyl, 2-propynyl (=propargyl) or 2-butynyl. Alkyl residues can also be unsaturated when they are substituted.

Examples of cycloalkyl having 3 to 10 carbon atoms are cycloalkyl residues containing 3, 4, 5, 6, 7, 8, 9, or 10 ring carbon atoms like cyclopropyl, cyclobutyl, cyclopentyl, cyclohexyl, cyloheptyl, cyclooctyl, cyclononyl or cyclodecyl, which can also be substituted and/or unsaturated. Unsaturated cyclic alkyl groups and unsaturated cycloalkyl groups like, for example, cyclopentenyl or cyclohexenyl can be bonded via any carbon atom.

Of course, a cyclic alkyl group has to contain at least three carbon atoms, and an unsaturated alkyl group has to contain at least two carbon atoms. Thus, a group like (C1-C8)-alkyl is to be understood as comprising, among others, saturated acyclic (C1-C8)-alkyl, (C3-C6)-cycloalkyl, and unsaturated (C2-C8)-alkyl like (C2-C8)-alkenyl or (C2-C8)-alkynyl. Similarly, a group like (C1-C4)-alkyl is to be understood as comprising, among others, saturated acyclic (C1-C4)-alkyl, and unsaturated (C2-C4)-alkyl like (C2-C4)-alkenyl or (C2-C4)-alkynyl.

Unless stated otherwise, the term alkyl preferably comprises acyclic saturated hydrocarbon residues which have from one to six carbon atoms and which can be linear or branched. A particular group of saturated acyclic alkyl residues is formed by (C1-C4)-alkyl residues like methyl, ethyl, n-propyl, isopropyl, n-butyl, isobutyl, sec-butyl and tBu.

The term "aryl" is understood as meaning aromatic hydrocarbon radicals containing from 6 to 14 carbon atoms in the ring. Examples of —(C6-C14)-aryl radicals are phenyl, naphthyl, for example 1-naphthyl and 2-naphthyl, biphenylyl, for example 2-biphenylyl, 3-biphenylyl and 4-biphenylyl, anthryl or fluorenyl. Biphenylyl radicals, naphthyl radicals and, in particular, phenyl radicals are preferred aryl radicals.

The terms "aralkyl" or "phenylalkyl" are understood as meaning an aryl residue, which is substituted by alkyl having 1 to 30 carbon atoms. Examples of arylalykl are benzyl, phenylethyl, phenylpropyl, naphthylmethyl or naphthylethyl. Examples of phenylalykl are benzyl, phenylethyl or phenylpropyl.

The terms "heterocycle", "heteroaryl" or "alicycle of heteroaryl" refer to heterocycles in which one or more of the 4 to 15 ring carbon atoms are replaced by heteroatoms such as nitrogen, oxygen or sulfur. Examples are acridinyl, azaindole (1H-pyrrolopyridinyl), azabenzimidazolyl, azaspirodecanyl, azepinyl, azetidinyl, aziridinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, carbazolyl, 4aH-carbazolyl, carbolinyl, chromanyl, chromenyl, cinnolinyl, decahydrochinolinyl, 4,5-dihydrooxazolinyl, dioxazolyl, dioxazinyl, 1,3-dioxolanyl, 1,3-dioxolenyl, 6H-1,5,2-dithiazinyl, dihydrofuro[2,3-b]-tetrahydrofuranyl, furanyl, furazanyl, imidazolidinyl, imidazolinyl, imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isothiazolidinyl, isothiazolinyl, isoxazolyl, isoxazolinyl, isoxazolidinyl, 2-isoxazolinyl, ketopiperazinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2-oxa-thiepanyl, 1,2-oxathiolanyl, 1,4-oxazepanyl, 1,2-oxazinyl, 1,3-oxazinyl, 1,4-oxazinyl, oxazolidinyl, oxazolinyl, oxazolyl, oxetanyl, oxocanyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazolyl, pyridinyl, pyridyl, pyrimidinyl, pyrrolidinyl, pyrrolidinonyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrahydrofuranyl, tetrahydropyranyl, tetrahydropyridinyl, tetrahydrothiophenyl, tetrazinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, 1,2-thiazinyl, 1,3-thiazinyl, 1,4-thiazinyl, 1,3-thiazolyl, thiazolyl, thiazolidinyl, thiazolinyl, thienyl, thietanyl, thienothiazolyl, thienooxazolyl, thienoimidazolyl, thietanyl, thiomorpholinyl, thiophenolyl, thiophenyl, thiopyranyl, 1,2,3-triazinyl, 1,2,4-triazinyl, 1,3,5-triazinyl, 1,2,3-triazolyl, 1,2,3-triazolyl, 1,2,4-triazolyl, 1,2,5-triazolyl, 1,3,4-triazolyl and xanthenyl. The fact that many of the before-listed names of heterocycles are the chemical names of unsaturated or aromatic ring systems does not imply that the 4-15 membered mono- or polycyclic group could only be derived from the respective unsaturated ring system. The names here only serve to describe the ring system with respect to ring size and the number of the heteroatoms and their relative positions. As explained above, the 4-15 membered mono- or polycyclic group can be saturated or partially unsaturated or aromatic, and can thus be derived not only from the before-listed heterocycles themselves but also from all their partially or completely hydrogenated analogues and also from their more highly unsaturated analogues if applicable. As examples of completely or partially hydrogenated analogues of the before-listed heterocycles from which this group may be derived the following may be mentioned: pyrroline, pyrrolidine, tetrahydrofuran, tetrahydrothiophene, dihydropyridine, tetrahydropyridine, piperidine, 1,3-dioxolane, 2-imidazoline, imidazolidine, 4,5-dihydro-1,3-oxazol, 1,3-oxazolidine, 4,5-dihydro-1,3-thiazole, 1,3-thiazolidine, perhydro-1,4-dioxane, piperazine, perhydro-1,4-oxazine (=morpholine), perhydro-1,4-thiazine (=thiomorpholine), perhydroazepine, indoline, isoindoline, 1,2,3,4-tetrahydroquinoline, 1,2,3,4-tetrahydroisoquinoline, etc.

The 4-15 membered mono- or polycyclic group may be bonded via any ring carbon atom, and in the case of nitrogen heterocycles via any suitable ring nitrogen atom. Thus, for example, a pyrrolyl residue can be 1-pyrrolyl, 2-pyrrolyl or 3-pyrrolyl, a pyrrolidinyl residue can be pyrrolidin-1-yl (=pyrrolidino), pyrrolidin-2-yl or pyrrolidin-3-yl, a pyridinyl residue, can be pyridin-2-yl, pyridin-3-yl or pyridin-4-yl, a piperidinyl residue can be piperidin-1-yl (=piperidino), piperidin-2-yl, piperidin-3-yl or piperidin-4-yl. Furyl can be 2-furyl or 3-furyl, thienyl can be 2-thienyl or 3-thienyl, imidazolyl can be imidazol-1-yl, imidazol-2-yl, imidazol-4-yl or imidazol-5-yl, 1,3-oxazolyl can be 1,3-oxazol-2-yl, 1,3-oxazol-4-yl or 1,3-oxazol-5-yl, 1,3-thiazolyl can be 1,3-thiazol-2-yl, 1,3-thiazol-4-yl or 1,3-thiazol-5-yl, pyrimidinyl can be pyrimidin-2-yl, pyrimidin-4-yl (=6-pyrimidinyl) or 5-pyrimidinyl, piperazinyl can be piperazin-1-yl (=piperazin-4-yl=piperazino) or piperazin-2-yl. Indolyl can be indol-1-yl, indol-2-yl, indol-3-yl, indol-4-yl, indol-5-yl, indol-6-yl or indol-7-yl. Similarly benzimidazolyl, benzoxazolyl and benzothiazol residues can be bonded via the 2-position and via any of the positions 4, 5, 6, and 7. Quinolinyl can be quinolin-2-yl, quinolin-3-yl, quinolin-4-yl, quinolin-5-yl, quinolin-6-yl, quinolin-7-yl or quinolin-8-yl, isoqinolinyl can be isoquinol-1-yl, isoquinolin-3-yl, isoquinolin-4-yl, isoquinolin-5-yl, isoquinolin-6-yl, isoquinolin-7-yl or isoquinolin-8-yl. In addition to being bonded via any of the positions indicated for quinolinyl and isoquinolinyl, 1,2,3,4-tetrahydroquinolinyl and 1,2,3,4-tetrahydroisoquinolinyl can also be bonded via the nitrogen atoms in 1-position and 2-position, respectively.

Unless stated otherwise, and irrespective of any specific substituents bonded to the 4-15 membered mono- or polycyclic group or any other heterocyclic groups which are indicated in the definition of the compounds of the formula I, the 4-15 membered mono- or polycyclic group can be unsubstituted or substituted on ring carbon atoms with one or more, for example one, two, three, four or five, identical or different substituents like (C1-C8)-alkyl, in particular (C1-C4)-alkyl, (C1-C8)-alkyloxy, in particular (C1-C4)-alkyloxy, (C1-C4)-alkylthio, halogen, nitro, amino, ((C1-C4)-alkyl)carbonylamino like acetylamino, trifluoromethyl, trifluoromethoxy, hydroxy, oxo, hydroxy-(C1-C4)-alkyl such as, for example, hydroxymethyl or 1-hydroxyethyl or 2-hydroxyethyl, methylenedioxy, ethylenedioxy, formyl, acetyl, cyano, aminosulfonyl, methylsulfonyl, hydroxycarbonyl, aminocarbonyl, (C1-C4)-alkyloxycarbonyl, optionally substituted phenyl, optionally substituted phenoxy, benzyl optionally substituted in the phenyl group, benzyloxy optionally substituted in the phenyl group, etc. The substituents can be present in any desired position provided that a stable molecule results. Of course an oxo group cannot be present in an aromatic ring. Each suitable ring nitrogen atom in the 4-15 membered mono- or polycyclic group can independently of each other be unsubstituted, i.e. carry a hydrogen atom, or can be substituted, i.e. carry a substituent like (C1-C8)-alkyl, for example (C1-C4)-alkyl such as methyl or ethyl, optionally substituted phenyl, phenyl-(C1-C4)-alkyl, for example benzyl, optionally substituted in the phenyl group, hydroxy-(C2-C4)-alkyl such as, for example 2-hydroxyethyl, acetyl or another acyl group, methylsulfonyl or another sulfonyl group, aminocarbonyl, (C1-C4)-alkyloxycarbonyl, etc. In general, in the compounds of the formula I nitrogen heterocycles can also be present as N-oxides or as quaternary salts. Ring sulfur atoms can be oxidized to the sulfoxide or to the sulfone. Thus, for example a tetrahydrothienyl residue may be present as S,S-dioxotetrahydro-thienyl residue or a thiomorpholinyl residue like thiomorpholin-4-yl may be present as 1-oxo-thiomorpholin-4-yl or 1,1-dioxo-thiomorpholin-4-yl. A substituted 4 to 15 membered mono- or polycyclic group that can be present in a specific position of the compounds of formulae I-4, I-8, I-9, I-10, I-12 or I-13 can independently of other groups be substituted by substituents selected from any desired subgroup of the substituents listed before and/or in the definition of that group.

The term "acyl" is understood as meaning an alkanoyl or aroyl, in which alkanoyl is straight or branched chain alkanoyl having 1 to 20 carbon atoms, such as formyl, acetyl, propionyl, butyryl, isobutyryl, pentanoyl, hexanoyl, heptanoyl or octanoyl, where alkanoyl may be substituted by phenyl.

The term "alkoxy" is understood as meaning a straight or branched chain alkoxy having 1 to 20 carbon atoms, such as methoxy, ethoxy, propoxy, butoxy, isobutoxy, pentyloxy, hexyloxy, heptyloxy or octyloxy.

The term "alkoxycarbonyl" is understood as meaning a straight or branched chain alkoxycarbonyl having 1 to 20 carbon atoms, such as methoxycarbonyl, ethoxycarbonyl, propoxycarbonyl, butoxycarbonyl, isobutoxycarbonyl, pentyloxycarbonyl, hexyloxycarbonyl, heptyloxycarbonyl or octyloxycarbonyl.

The term "alkylamino" is understood as meaning a straight or branched chain alkyl having 1 to 20 carbon atoms, such as methylamino, ethylamino, propylamino, butylamino, isobutylamino, pentylamino, hexylamino, heptylamino or octylamino.

The term "alkylthio" is understood as meaning a straight or branched chain alkyl having 1 to 20 carbon atoms, such as methylthio, ethylthio, propylthio, butylthio, isobutylthio, pentylthio, hexylthio, heptylthio or octylthio.

The term "acylamino" is understood as meaning an acyl moiety, in which acyl is straight or branched chain alkanoyl having 1 to 20 carbon atoms, such as formylamino, acetylamino, propionylamino, butyrylamino, isobutyrylamino, pentanoylamino, hexanoylamino, heptanoylamino or octanoylamino, where alkanoyl may be substituted by phenyl. Halogen is fluorine, chlorine, bromine or iodine, preferably fluorine, chlorine or bromine, particularly preferably chlorine or bromine.

The term "alkylcarbamoyl" is understood as meaning a straight or branched chain alkyl having 1 to 20 carbon atoms, such as methylcarbamoyl, ethylcarbamoyl, propylcarbamoyl, butylcarbamoyl, isobutylcarbamoyl, pentylcarbamoyl, hexylcarbamoyl, heptylcarbamoyl or octylcarbamoyl.

The term "aryloxy" is understood as meaning phenoxy or naphthyloxy.

The term "alkoxycarbonylamino" is understood as meaning a straight or branched chain alkoxycarbonyl having 1 to 20 carbon atoms, such as methoxycarbonylamino, ethoxycarbonylamino, propoxycarbonylamino, butoxycarbonylamino, isobutoxycarbonylamino, pentyloxycarbonylamino, hexyloxycarbonylamino, heptyloxycarbonylamino or octyloxycarbonylamino.

The term "acyloxy" is understood as meaning an alkanoyl or aroyl, in which alkanoyl is straight or branched chain alkanoyl having 1 to 20 carbon atoms, such as acetoxy, propionyloxy, butyryloxy, isobutyryloxy, pentanoyloxy, hexanoyloxy, heptanoyloxy or octanoyloxy, where alkanoyl may be substituted by phenyl.

The term "pain" describes acute and chronic pain states.

Examples for chronic pain states are:

Chronic muscular diseases such as back pain, pain during menstruation, pain during osteoarthritis, pain during rheumatoid arthritis, pain during gastrointestinal inflammation, pain during inflammation of the heart muscle, pain during multiple sclerosis, pain during neuritis, pain during AIDS, pain during chemotherapy, tumor pain, neuropathic pain e.g. after amputation, trigeminal neuralgia, migraine or post herpetic neuralgia.

Examples for acute pain are:

Pain after injuries, Postoperative pain, Pain during acute gout, Pain during operations, such as jaw surgery.

Optically active carbon atoms present in the compounds of the formulae I-4, I-8, I-9, I-10, I-12 or I-13 can independently of each other have R configuration or S configuration. The compounds of the formulae I-4, I-8, I-9, I-10, I-12 or I-13 can be present in the form of pure enantiomers or pure diastereomers or in the form of mixtures of enantiomers and/or diastereomers, for example in the form of racemates. The present invention relates to pure enantiomers and mixtures of enantiomers as well as to pure diastereomers and mixtures of diastereomers. The invention comprises mixtures of two or of more than two stereoisomers of the formulae I-4, I-8, I-9, I-10, I-12 or I-13, and it comprises all ratios of the stereoisomers in the mixtures. In case the compounds of the formulae I-4, I-8, I-9, I-10, I-12 or I-13 can be present as E isomers or Z isomers (or cis isomers or trans isomers) the invention relates both to pure E isomers and pure Z isomers and to E/Z mixtures in all ratios. The invention also comprises all tautomeric forms of the compounds of the formulae I-4, I-8, I-9, I-10, I-12 or I-13.

Diastereomers, including E/Z isomers, can be separated into the individual isomers, for example, by chromatography. Racemates can be separated into the two enantiomers by customary methods, for example by chromatography on chiral phases or by resolution, for example by crystallization of diastereomeric salts obtained with optically active acids or bases. Stereochemically uniform compounds of the formulae I-4, I-8, I-9, I-10, I-12 or I-13 can also be obtained by employing stereochemically uniform starting materials or by using stereoselective reactions.

Physiologically tolerable salts of the compounds of formulae I-4, I-8, I-9, I-10, I-12 or I-13 are nontoxic salts that are physiologically acceptable, in particular pharmaceutically utilizable salts. Such salts of compounds of the formulae I-4, I-8, I-9, I-10, I-12 or I-13 containing acidic groups, for example a carboxyl group COOH, are for example alkali metal salts or alkaline earth metal salts such as sodium salts, potassium salts, magnesium salts and calcium salts, and also salts with physiologically tolerable quaternary ammonium ions such as tetramethylammonium or tetraethylammonium, and acid addition salts with ammonia and physiologically tolerable organic amines, such as methylamine, dimethylamine, trimethylamine, ethylamine, triethylamine, ethanolamine or tris-(2-hydroxyethyl)amine. Basic groups contained in the compounds of the formulae I-4, I-8, I-9, I-10, I-12 or I-13, for example carbamoyl groups or guanidino groups, form acid addition salts, for example with inorganic acids such as hydrochloric acid, hydrobromic acid, sulfuric acid, nitric acid or phosphoric acid, or with organic carboxylic acids and sulfonic acids such as formic acid, acetic acid, oxalic acid, citric acid, lactic acid, malic acid, succinic acid, malonic acid, benzoic acid, maleic acid, fumaric acid, tartaric acid, methanesulfonic acid or p-toluenesulfonic acid or amino acids such as lysine salts. Compounds of the formulae I-4, I-8, I-9, I-10, I-12 or I-13, which simultaneously contain a basic group and an acidic group, for example a guanidino group and a carboxyl group, can also be present as zwitterions (betaines), which are likewise included in the present invention.

Salts of compounds of the formulae I-4, I-8, I-9, I-10, I-12 or I-13 can be obtained by customary methods known to those skilled in the art, for example by combining a compound of the formulae I-4, I-8, I-9, I-10, I-12 or I-13 with an inorganic or organic acid or base in a solvent or dispersant, or from other salts by cation exchange or anion exchange. The present invention also includes all salts of the compounds of the formulae I-4, I-8, I-9, I-10, I-12 or I-13 which, because of low physiologically tolerability, are not directly suitable for use in pharmaceuticals but are suitable, for example, as intermediates for carrying out further chemical modifications of the compounds of the formulae I-4, I-8, I-9, I-10, I-12 or I-13 or as starting materials for the preparation of physiologically tolerable salts.

The present invention furthermore includes all solvates of compounds of the formulae I-4, I-8, 1-9, I-10, I-12 or I-13, for example hydrates or adducts with alcohols.

In general compounds of the formulae I-4, I-8, I-9, I-10, I-12 or I-13 can be prepared as described in EP 0 627 406.

The compounds of the present invention are S1P-receptor agonists and thus the compounds of the formulae I-4, I-8, I-9, I-10, I-12 or I-13 can be used for decreasing pain.

The pharmaceuticals can be administered orally, for example in the form of pills, tablets, lacquered tablets, coated tablets, granules, hard and soft gelatin capsules, solutions, syrups, emulsions, suspensions or aerosol mixtures. Administration, however, can also be carried out rectally, for example in the form of suppositories, or parenterally, for example intravenously, intramuscularly or subcutaneously, in the form of injection solutions or infusion solutions, microcapsules, implants or rods, or percutaneously or topically, for example in the form of ointments, solutions or tinctures, or in other ways, for example in the form of aerosols or nasal sprays or transdermal patches.

The pharmaceutical preparations according to the invention are prepared in a manner known per se and familiar to one skilled in the art, pharmaceutically acceptable inert inorganic and/or organic carriers being used in addition to the compound(s) of the formulae I-4, I-8, I-9, I-10, I-12 or I-13 and/or its (their) physiologically tolerable salts. For the production of pills, tablets, coated tablets and hard gelatin capsules it is possible to use, for example, lactose, cornstarch or derivatives thereof, talc, stearic acid or its salts, etc. Carriers for soft gelatin capsules and suppositories are, for example, fats, waxes, semisolid and liquid polyols, natural or hardened oils, etc. Suitable carriers for the production of solutions, for example injection solutions, or of emulsions or syrups are, for example, water, saline, alcohols, glycerol, polyols, sucrose, invert sugar, glucose, vegetable oils, etc. Suitable carriers for microcapsules, implants or rods are, for example, copolymers of glycolic acid and lactic acid. The pharmaceutical preparations normally contain about 0.5% to 90% by weight of the compounds of the formulae I-4, I-8, I-9, I-10, I-12 or I-13 and/or their physiologically tolerable salts. The amount of the active ingredient of the formulae I-4, I-8, I-9, I-10, I-12 or I-13 and/or its physiologically tolerable salts in the pharmaceutical preparations normally is from about 0.5 mg to about 1000 mg, preferably from about 1 mg to about 500 mg.

In addition to the active ingredients of the formulae I-4, I-8, I-9, I-10, I-12 or I-13 and/or their physiologically acceptable salts and to carrier substances, the pharmaceutical preparations can contain additives such as, for example, fillers, disintegrants, binders, lubricants, wetting agents, stabilizers, emulsifiers, preservatives, sweeteners, colorants, flavorings, aromatizers, thickeners, diluents, buffer substances, solvents, solubilizers, agents for achieving a depot effect, salts for altering the osmotic pressure, coating agents or antioxidants. They can also contain two or more compounds of the formulae I-4, I-8, I-9, I-10, I-12 or I-13 and/or their physiologically tolerable salts. In case a pharmaceutical preparation contains two or more compounds of the formulae I-4, I-8, I-9, I-10, I-12 or I-13 the selection of the individual compounds can aim at a specific overall pharmacological profile of the pharmaceutical preparation. For example, a highly potent compound with a shorter duration of action may be combined with a long-acting compound of lower potency. The flexibility permitted with respect to the choice of substituents in the compounds of the formulae I-4, I-8, I-9, I-10, I-12 or I-13 allows a great deal of control over the biological and physicochemical properties of the compounds and thus allows the selection of such desired compounds. Furthermore, in addition to at least one compound of the formulae I-4, I-8, I-9, I-10, I-12 or I-13 and/or its physiologically tolerable salts, the pharmaceutical preparations can also contain one or more other therapeutically or prophylactic ally active ingredients.

It is understood that changes that do not substantially affect the activity of the various embodiments of this invention are included within the invention disclosed herein. Thus, the following examples are intended to be merely illustrative of the present invention, and not limiting thereof in either scope or spirit.

EXAMPLES

Example 1

Determination of the Analgesic Effect of S1P

The analgesic effect of sphingosine-1-phosphate (S1P) was determined by intrathecal application to the spinal cord by:

a) Implantation of Lumbar Intrathecal Catheters:

Wild type Sprague Dawley rats were purchased from Charles River Wiga GmbH (Sulzfeld, Germany). The animals had free access to food and water prior to the experiments. They were maintained in climate- and light-controlled rooms (24+0.5° C.). Each animal was used at one occasion only. In all experiments the ethics guidelines for investigations in conscious animals were obeyed, and the procedures were approved by the local Ethics Committee.

Rats were anesthetized with ketamine (60 mg/kg i.p.) and midazolam (0.5 to 1 mg/kg i.p.). The skin was incised above the vertebral column from vertebrae Th13 up to L3. Muscle tissue around L2-3 was cleared away. The processus spinosus of L3 was removed and a laminectomy was done at L2. Polyethylene catheters (ID 0.28 mm, OD 0.61 mm) were then inserted into the peridural space so that the tip of the catheter reached Th9-10. The catheter was fixed with cyanacrylate glue and was externalized in the neck region and the skin was sutured.

b) Infusion of PAM Oligonucleotides:

Three days after surgery rats were placed into a "freely moving system" (CMA, Stockholm, Sweden) 20 µl of 10 µM S1P, purchased from Tocris (Ellisville, Mo.), were infused through the catheter.

c) Formalin Test:

Within 15 min after stopping the infusion the formalin test was performed. 50 µL of a 5% formaldehyde solution were injected subcutaneously (s. c.) into the dorsal surface of one hind paw. Flinches were counted in one-minute intervals up to 60 min starting right after formalin injection. Flinches of 5 min intervals were summarized as mean flinches per minute. To compare the nociceptive behavior between groups the sum of flinches during the one-hour observation period were submitted to the Students t-test.

At the end of the formalin test, the rats were killed.

d) Results:

S1P was dissolved in DMSO to a final concentration of 2.5 mM and then diluted 1:250 in PBS. 20 µl of 10 µM S1P or 20 µl 0.1 M phosphate buffered saline, pH 7.2 (PBS,) in DMSO were given to adult rats by intrathecal application 15 minutes prior to the formalin injection. Then, flinches were counted in 5 minutes intervals over a period of 60 minutes.

A significant decrease in the number of nociceptive responses for phase 2A, which is the time from 20 to 35 minutes after formalin injection, could be detected as compared to PBS/DMSO-treated animals. These experiments clearly demonstrated that exogenous S1P acts as an analgesic.

Table 1 shows the results of the mean of six animal experiments +SEM.

TABLE 1

| Time (min) | Mean control | SEM control | Mean S1P 10 µM | SEM S1P 10 µM |
|---|---|---|---|---|
| 5 | 68.0 | 11.4 | 60.9 | 9.6 |
| 10 | 29.3 | 4.1 | 24.6 | 5.7 |
| 15 | 23.8 | 5.3 | 12.7 | 3.0 |
| 20 | 41.5 | 6.5 | 17.1 | 3.4 |
| 25 | 54.1 | 12.0 | 19.6 | 5.1 |
| 30 | 68.3 | 10.4 | 24.7 | 5.5 |
| 35 | 74.7 | 12.5 | 31.4 | 5.5 |
| 40 | 58.0 | 4.0 | 41.9 | 6.6 |
| 45 | 64.9 | 6.0 | 49.3 | 9.8 |
| 50 | 60.7 | 9.0 | 41.3 | 9.6 |
| 55 | 58.5 | 5.2 | 49.0 | 9.7 |
| 60 | 53.7 | 12.9 | 38.0 | 7.9 |

Example 2

Determination of the Analgesic Effect of 2-amino-2-[2-(4-octylphenyl)ethyl]-1,3-propanediol Hydrochloride Animals: Male Sprague Dawley rats weighing 300-350 g were purchased from Charles River Wiga GmbH (Sulzfeld, Germany). The animals had free access to food and water prior to the experiments. They were maintained in climate- and light-controlled rooms (24+0.5° C.). Each animal was used at one occasion only. In all experiments the ethics guidelines for investigations in conscious animals were obeyed and the procedures were approved by the local Ethics Committee.

Formalin test: The formalin assay was performed in a dedicated room with restriction on sound level and activity. 2-amino-2-[2-(4-octylphenyl)ethyl]-1,3-propanediol hydrochloride (compound 1) was dissolved in polyethylene-glycol (PEG) at a concentration of 1 mg/ml and injected interiperitoneally (1 mg/kg) 3 hours prior to the formalin tests were performed with compound 1. 50 µl of a 5% formaldehyde solution was injected subcutaneously (s.c.) into the dorsal surface of one hind paw. Rats were placed into a plexiglas chamber surrounded by mirrors to allow an unobstructed view of the paws. Flinches were counted in one-minute intervals up to 60 min starting right after formalin injection. Flinches of 5 min intervals were summarized as mean flinches per minute +SEM. Statistical analysis was performed using the student's t-test (*$p<0.04$).

A significant decrease in the number of nociceptive responses for phase 2A, which is the time from 20 to 35 minutes after formalin injection, could be detected as compared to the control animals (four animals). These experiments clearly demonstrated that compound 1 is an analgesic.

Table 2 shows the results of the mean of five animal experiments +SEM.

TABLE 2

| Time (min) | Compound 1 (1 mg/kg) | SEM (compound 1) | Control | SEM (control) |
|---|---|---|---|---|
| 5 | 85.4 | 13.2 | 95.0 | 3.4 |
| 10 | 41.2 | 4.9 | 29.0 | 6.7 |
| 15 | 33.6 | 6.3 | 40.8 | 1.7 |
| 20 | 29.6 | 7.2 | 41.0 | 5.4 |
| 25 | 31.6 | 4.1 | 61.5 | 4.5 |
| 30 | 51.4 | 13.1 | 72.0 | 9.0 |
| 35 | 49.2 | 4.8 | 69.0 | 6.4 |
| 40 | 48.0 | 5.8 | 76.3 | 5.6 |
| 45 | 48.6 | 10.7 | 67.5 | 7.9 |
| 50 | 39.8 | 4.6 | 45.5 | 5.5 |
| 55 | 42.6 | 13.3 | 38.5 | 5.9 |
| 60 | 42.2 | 5.0 | 37.0 | 4.4 |

Compound 1 n = 5 rats
control n = 4 rats

Example 3

Determination of the Analgesic or Antinociceptive Effect of a S1P Receptor Agonist The analgesic or antinociceptive effect of a compound of the formulae I-4, I-8, I-9, I-10, I-12 or I-13 can be determined in the formalin model of acute pain as described in example 1. The effect of a compound of the formulae I-4, I-8, I-9, I-10, I-12 or I-13 can be determined either by inthathecal, intravenous, subcutaneous, interperitoneal, topical or oral application and consecutive testing of its analgesic or antinociceptive effect by means of the flinch test. This approach allows the molecule to enter the tissue and mimic the actions of physiological S1P towards adenylate cyclase.

The invention claimed is:

1. A method for the treatment of acute pain, said method comprising administering to a patient in need thereof an effective amount of a 2-amino-1,3-propanediol compound of formula I-4

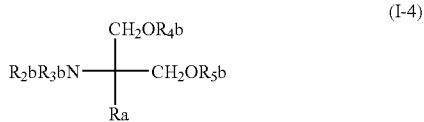

wherein:
Ra is a straight- or branched chain alkyl having 12 to 22 carbon atoms, said alkyl chain being unsubstituted or substituted in the chain by a substituent selected from the group consisting of double bonds, triple bonds and hetero atom-containing substituents selected from oxygen, sulfinyl, sulfonyl, sulfur, —N(R6)- where R6 is selected from hydrogen, acyl, alkoxycarbonyl, alkyl and aralkyl: said alkyl chain being optionally further substituted by one or more of acyl, acylamino, alkenyloxy, alkoxy, alkoxycarbonyl, alkoxycarbonylamino, alkylamino, alkylcarbamoyl, alkylthio, alkynyloxy, amino, aralkyloxy, aralkyloxyacyloxy, carboxyl, halogen, hydroxyl, hydroxyimino and nitro; and R2b, R3b, R4b and R5b are the same or different and each is selected from hydrogen, acyl and alkyl;
or a pharmaceutically acceptable salt thereof.

2. A method for the treatment of acute pain, said method comprising administering to a patient in need thereof an effective amount of a 2-amino-1,3-propanediol compound of formula I-8,

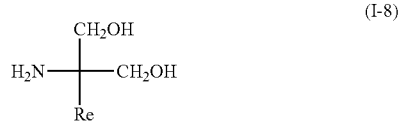

wherein
Re is selected from the group consisting of phenylalkyl, wherein the alkyl moiety is a straight- or branched chain having 6 to 20 carbon atoms; phenylalkyl, wherein the alkyl moiety is a straight- or branched chain alkyl having 1 to 30 carbon atoms, said phenylalkyl being substituted by a straight- or branched chain C6-C20 alkyl optionally substituted by halogen, a straight- or branched chain C6-C20 alkoxy optionally substituted by halogen, a straight- or branched chain C6-C20 alkenyloxy, phenylalkoxy, halophenyl alkoxy, phenylalkoxyalkyl, phenoxyalkoxy or phenoxyalkyl; a cycloalkylalkyl wherein the alkyl moiety is a straight- or branched chain having 6 to 20 carbon atoms; a cycloalkylalkyl substituted by a straight- or branched chain alkyl having 6 to 20 carbon atoms; a heteroarylalkyl wherein the alkyl moiety is a straight- or branched chain having 6 to 20 carbon atoms; a heteroarylalkyl substituted by a straight- or branched chain alkyl having 6 to 20 carbon atoms; a heterocyclic alkyl wherein the alkyl moiety is a straight- or branched chain having 6 to 20 carbon atoms; or a heterocyclic alkyl substituted by a straight- or branched chain alkyl having 6 to 20 carbon atoms; wherein the alkyl moiety may have, in the carbon chain, a bond or a hetero atom selected from a double bond, a triple bond, oxygen, sulfur, sulfonyl, —N(R6)-(where R6 is hydrogen, alkyl, aralkyl, acyl or alkoxycarbonyl), and carbonyl, and may have as a substituent, alkoxy, alkenyloxy, alkynyloxy, aralkyloxy, acyl, alkylamino, alkylthio, acylamino, alkoxycarbonyl, alkoxycarbonylamino, acyloxy, alkylcarbamoyl, nitro, halogen, amino, hydroxyl or carboxyl; or a pharmaceutically acceptable salt thereof.

3. A method for the treatment of acute pain, said method comprising administering to a patient in need thereof an effective amount of a 2-amino-1,3-propanediol compound of formula I-9,

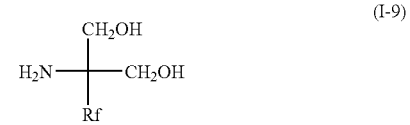

wherein Rf is a phenylalkyl wherein the alkyl moiety is a straight- or branched chain having 6 to 20 carbon atoms which may have, in the carbon chain, one or two oxygen atoms; a phenylalkyl, wherein the alkyl moiety is a straight- or branched chain alkyl having 1 to 30 carbon atoms, said phenylalkyl being substituted by a straight- or branched chain C6-C20 alkyl optionally substituted by halogen, a straight- or branched chain C6-C20 alkoxy optionally substituted by halogen, a straight- or branched chain C6-C20 alkenyloxy, phenylalkoxy, halophenyl alkoxy, phenylalkoxyalkyl, phenoxy alkoxy or phenoxyalkyl; a cycloalkylalkyl wherein the alkyl moiety is a straight- or branched chain having 6 to 20 carbon atoms which may have, in the carbon chain, one or two oxygen atoms; a cycloalkylalkyl substituted by a straight- or branched chain alkyl having 6 to 20 carbon atoms; a heteroarylalkyl wherein the alkyl moiety is a straight- or branched chain having 6 to 20 carbon atoms which may have, in the carbon chain, one or two oxygen atoms; a heteroarylalkyl substituted by a straight- or branched chain alkyl having 6 to 20 carbon atoms; a heterocyclic alkyl wherein the alkyl moiety is a straight- or branched chain having 6 to 20 carbon atoms which may have, in the carbon chain, one or two oxygen atoms; or a heterocyclic alkyl substituted by a straight- or branched chain alkyl having 6 to 20 carbon atoms;
wherein the alkyl moiety has in the carbon chain a substituent selected from alkoxy, alkenyloxy, alkynyloxy, aralkyloxy, acyl, alkylamino, alkylthio, alkoxycarbonyl, alkoxycarbonylamino, acyloxy, alkylcarbamoyl, nitro, halogen, amino, hydroxyl and carboxyl; or a pharmaceutically acceptable salt thereof.

4. The method of claim 2 wherein said 2-amino-1,3-propanediol compound is a compound of formula I-10,

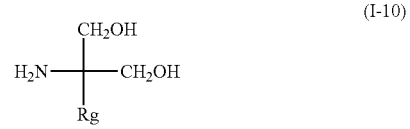

wherein
Rg is a phenylalkyl wherein the alkyl moiety is a straight- or branched chain having 6 to 20 carbon atoms which may have, in the carbon chain, one or two oxygen atoms; a phenylalkyl, wherein the alkyl moiety is a straight- or branched chain alkyl having 1 to 30 carbon atoms, said phenylalkyl being substituted by a straight- or branched chain C6-C14 alkyl optionally substituted by halogen, a straight- or branched chain C6-C14 alkoxy optionally substituted by halogen, a straight- or branched chain C6-C14 alkenyloxy, phenylalkoxy, halo-phenylalkoxy, phenyl-alkoxyalkyl, phenoxy-alkoxy or phenoxy-alkyl; a cycloalkylalkyl wherein the alkyl moiety has 6 to 20 carbon atoms; a cycloalkylalkyl substituted by a straight- or branched chain alkyl having 6 to 14 carbon atoms; a heteroarylalkyl wherein the alkyl moiety has 6 to 20 carbon atoms; a heteroarylalkyl substituted by a straight- or branched chain alkyl having 6 to 14 carbon atoms; a heterocyclic alkyl wherein the alkyl moiety has 6 to 20 carbon atoms; or a heterocyclic alkyl substituted by a straight- or branched chain alkyl having 6 to 14 carbon atoms; or a pharmaceutically acceptable salt thereof.

5. A method for the treatment of acute pain, said method comprising administering to a patient in need thereof an effective amount of a 2-amino-1,3-propanediol compound is a compound of formula I-12,

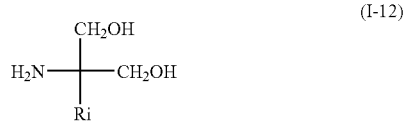

(I-12)

wherein

Ri is a phenylalkyl, wherein the alkyl moiety is a straight- or branched chain alkyl having 1 to 30 carbon atoms, said phenylalkyl being substituted by a straight- or branched chain C6-C14 alkyl optionally substituted by halogen, a straight- or branched chain C6-C14 alkoxy optionally substituted by halogen or a straight- or branched chain C6-C14 alkenyloxy, wherein the alkyl moiety of phenylalkyl may be substituted by hydroxyl; or a pharmaceutically acceptable salt thereof.

6. The method of claim 5 wherein said 2-amino-1,3-propanediol compound is a compound of formula I-13,

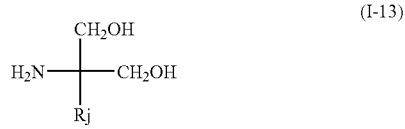

(I-13)

wherein

Rj is a phenylalkyl, wherein the alkyl moiety is a C2-C6 alkyl optionally substituted by hydroxyl, said phenylalkyl being substituted by a straight- or branched chain C6-C14 alkyl optionally substituted by halogen, a straight- or branched chain C6-C14 alkoxy optionally substituted by halogen, or a straight- or branched chain C6-C14 alkenyloxy, or a pharmaceutically acceptable salt thereof.

7. A method for the treatment of acute pain, said method comprising administering to a patient in need thereof an effective amount of a 2-amino-1,3-propanediol compound selected from the group consisting of:
2-amino-2-[2-(4-heptylphenyl)ethyl]-1,3-propanediol,
2-amino-2-[2-(4-octylphenyl)ethyl]-1,3-propanediol,
2-amino-2-[2-(4-octylphenyl)ethyl]-1,3-propanediol hydrochloride,
2-amino-2-[2-(4-nonylphenyl)ethyl]-1,3-propanediol,
2-amino-2-[2-(4-decylphenyl)ethyl]-1,3-propanediol,
2-amino-2-[2-(4-undecylphenyl)ethyl]-1,3-propanediol,
2-amino-2-[2-(4-dodecylphenyl)ethyl]-1,3-propanediol,
2-amino-2-[2-(4-tridecylphenyl)ethyl]-1,3-propanediol,
2-amino-2-[2-(4-tetradecylphenyl)ethyl]-1,3-propanediol,
2-amino-2-[2-(4-hexyloxyphenyl)ethyl]-1,3-propanediol,
2-amino-2-[2-(4-heptyloxyphenyl)ethyl]-1,3-propanediol,
2-amino-2-[2-(4-octyloxyphenyl)ethyl]-1,3-propanediol,
2-amino-2-[2-(4-nonyloxyphenyl)ethyl]-1,3-propanediol,
2-amino-2-[2-(4-decyloxyphenyl)ethyl]-1,3-propanediol,
2-amino-2-[2-(4-undecyloxyphenyl)ethyl]-1,3-propanediol,
2-amino-2-[2-(4-dodexyloxyphenyl)ethyl]-1,3-propanediol,
2-amino-2-[2-(4-tridecyloxyphenyl)ethyl]-1,3-propanediol,
2-amino-2-[2-(4-(8-fluorooctyl)phenyl)ethyl]-1,3-propanediol,
2-amino-2-[2-(4-(12-fluorododecyl)phenyl)ethyl]-1,3-propanediol,
2-amino-2-[2-(4-(7-fluoroheptyloxy)phenyl)ethyl]-1,3-propanediol,
2-amino-2-[2-(4-(11-fluoroundecyloxy)phenyl)ethyl]-1,3-propanediol and
2-amino-2-[2-(4-(7-octenyloxy)phenyl)ethyl]-1,3-propanediol, and the pharmaceutically acceptable salts thereof.

8. The method of claim 1 for the treatment of acute pain, wherein said acute pain is selected from pain occurring after injuries, postoperative pain, pain occurring during acute gout, and pain occurring during operations.

9. The method of claim 2 for the treatment of acute pain, wherein said acute pain is selected from pain occurring after injuries, postoperative pain, pain occurring during acute gout, and pain occurring during operations.

10. The method of claim 3 for the treatment of acute pain, wherein said acute pain is selected from pain occurring after injuries, postoperative pain, pain occurring during acute gout, and pain occurring during operations.

11. The method of claim 5 for the treatment of acute pain, wherein said acute pain is selected from pain occurring after injuries, postoperative pain, pain occurring during acute gout, and pain occurring during operations.

12. The method of claim 7 for the treatment of acute pain, wherein said acute pain is selected from pain occurring after injuries, postoperative pain, pain occurring during acute gout, and pain occurring during operations.

* * * * *